United States Patent
Fontana et al.

(10) Patent No.: US 9,606,089 B2
(45) Date of Patent: Mar. 28, 2017

(54) METHODS FOR DETECTING AND REDUCING IMPURITIES OF LAPATINIB AND SALTS THEREOF

(71) Applicant: F.I.S.—Fabbrica Italiana Sintetici S.p.A., Alte di Montecchio Maggiore (IT)

(72) Inventors: Francesco Fontana, Alte di Montecchio Maggiore (IT); Alessandro Leganza, Alte di Montecchio Maggiore (IT); Sergio Osti, Alte di Montecchio Maggiore (IT)

(73) Assignee: F.I.S.—FABBRICA ITALIANA SINTETICI S.P.A., Alte di Montecchio Maggiore (Vicenza) (IT)

( * ) Notice: Subject to any disclaimer, the term of this patent is extended or adjusted under 35 U.S.C. 154(b) by 435 days.

(21) Appl. No.: 14/482,770

(22) Filed: Sep. 10, 2014

(65) Prior Publication Data

US 2015/0260696 A1 Sep. 17, 2015

Related U.S. Application Data

(62) Division of application No. 13/470,411, filed on May 14, 2012, now Pat. No. 8,927,558.

(30) Foreign Application Priority Data

May 20, 2011 (IT) ................ MI2011A0894

(51) Int. Cl.

| A61K 31/517 | (2006.01) |
|---|---|
| C07D 405/10 | (2006.01) |
| G01N 30/86 | (2006.01) |
| G01N 30/06 | (2006.01) |

(52) U.S. Cl.
CPC ......... *G01N 30/8631* (2013.01); *G01N 30/06* (2013.01)

(58) Field of Classification Search
CPC ..................... G01N 30/8631; G01N 30/06
USPC ..................... 514/266.22; 544/284
See application file for complete search history.

(56) References Cited

U.S. PATENT DOCUMENTS

| 6,727,256 B1 | 4/2004 | Carter et al. |
|---|---|---|
| 2002/0147205 A1 | 10/2002 | Carter et al. |
| 2003/0176451 A1 | 9/2003 | Carter et al. |
| 2003/0220354 A1 | 11/2003 | McClure et al. |
| 2005/0130996 A1 | 6/2005 | Carter et al. |
| 2007/0015775 A1 | 1/2007 | Carter et al. |
| 2007/0238875 A1 | 10/2007 | Carter et al. |
| 2009/0203718 A1 | 8/2009 | Rusnak et al. |
| 2010/0120804 A1 | 5/2010 | Carter et al. |
| 2010/0197915 A1 | 8/2010 | Metsger et al. |

*Primary Examiner* — Paul V Ward
(74) *Attorney, Agent, or Firm* — Lucas & Mercanti LLP

(57) ABSTRACT

Impurities of lapatinib such as N-{3-chloro-4-[(2-fluorobenzyl)oxy]phenyl}-6-[5-({[2-(methylsulfonyl)ethyl]amino}methyl)furan-2-yl]quinazoline-4-amine compound of formula (I) or a salt thereof:

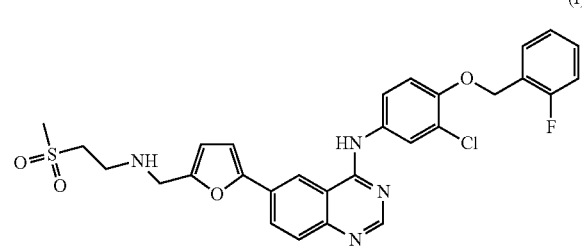

(I)

and analytical methods for identifying and quantifying such impurities of Lapatinib and salts thereof are provided. Also provided is Lapatinib containing less than about 0.05 percent of this and related impurities and methods for preparing such pure forms of Lapatinib.

4 Claims, 8 Drawing Sheets

METHODS FOR DETECTING AND REDUCING IMPURITIES OF LAPATINIB AND SALTS THEREOF

CROSS REFERENCE TO RELATED APPLICATION

This application is a Divisional of U.S. patent application Ser. No. 13/470,411 filed May 14, 2012, which claims priority to and benefit of Italian Patent Application No. MI2011A000894 filed May, 20 2011, the contents of each of which are incorporated by reference in their entirety.

FIELD OF THE INVENTION

The present invention relates to impurities of the active ingredient Lapatinib, methods for identifying, quantifying and preventing or limiting the presence thereof in Lapatinib and salts thereof.

BACKGROUND OF THE INVENTION

Lapatinib is a pharmaceutically active ingredient used for the treatment of advanced metastatic lung cancer and is currently available on the market under the name Tykerb® sold by GlaxoSmithKline (GSK).

According to the indications of the manufacturer, Tykerb® contains Lapatinib as a monohydrate ditosylate salt of formula (XIII-bis):

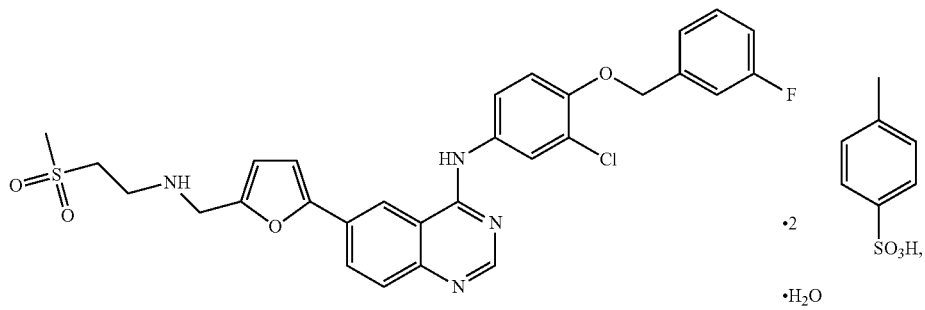

having the chemical name of N-{3-chloro-4-[(3-fluorobenzyl)oxy]phenyl}-6-[5-({[2-(methylsulfonyl)ethyl]amino}methyl)furan-2-yl]quinazoline-4-amine bis(4-methylbenzenesulfonate) monohydrate, CAS RN 388082-78-8 and melting point 250-256° C.

This substance may be prepared using methods described for example in U.S. Pat. No. 7,157,466. Examples 10 and 11 of this reference show the preparation of monohydrate ditosylate salt starting from anhydrous ditosylate salt.

Like other compounds obtained by means of chemical synthesis, Lapatinib, or salts thereof, may contain small amounts of impurities. These impurities may be raw materials, synthetic intermediates, reaction by-products, product degradation products, and the like. Pharmaceutical impurities, may affect both the efficiency and the safety of a drug which, in extreme cases, could be harmful for the patient. The purity of an active ingredient like Lapatinib produced through a production process based on subsequent chemical reactions represents a critical factor with respect to commercialization. The United States Food and Drug Administration (FDA) and the European Medicinal Agency (EMA) (as well as their respective pharmacopoeia) require that impurities be maintained below given limits.

The product of a chemical reaction rarely involves a single compound having purity sufficient to meet regulatory standards. By-products due to secondary reactions of reagents also can be present in the isolated product. In certain steps of the production process of an active ingredient, such as Lapatinib, the purity may be analysed, generally by methods such as high performance liquid chromatography (HPLC), gas chromatography (GC) or thin layer chromatography (TLC), to determine whether the active ingredient is suitable for subsequent treatment and for use in the final pharmaceutical product. Generally, impurities are identified spectroscopically and provide a chromatographic peak on a chromatogram or as a spot on a TLC panel.

Once a peak position has been associated with a particular impurity, the impurity can be identified in a sample based on its position in the chromatogram, where the position in the chromatogram is measured in minutes between the injection of the sample in a column and elution of the impurity through the detector. The position in the chromatogram is known as the retention time and the ratio between the retention times is known as the relative retention time.

A relatively pure compound may be used as a reference standard. A reference standard is similar to a reference marker, except that the latter can be used not only for detecting impurities, but also for quantifying the amount of impurities present in the sample.

Impurities of Lapatinib, including intermediaries not entirely reacted, impurities of the raw materials, the reaction by-products, degradation products, as well as other products, may affect the quality and efficiency of the pharmaceutical form containing Lapatinib. Thus, there is a great need for methods of defining the level of impurities in samples of Lapatinib and methods for removing impurities, limiting the content thereof or preventing the formation thereof.

SUMMARY OF THE INVENTION

The present invention relates to N-{3-chloro-4-[(2-fluorobenzyl)oxy]phenyl}-6-[5-({[2-(methylsulfonyl)ethyl]amino}methyl)furan-2-yl]quinazoline-4-amine compound of formula (I) or a salt thereof:

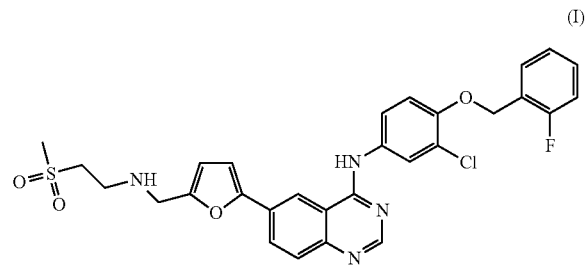 [SMILES: CS(=O)(=O)CCNCc1ccc(-c2ccc3ncnc(Nc4ccc(OCc5ccccc5F)c(Cl)c4)c3c2)o1]

and analytical methods for detecting and quantifying this impurity in Lapatinib and salts thereof, as well as methods of preparation and use thereof. The present invention also provides methods of synthesis of Lapatinib having low levels of impurities and in some embodiments less than 0.05% weight of the compound of formula (I).

DETAILED DESCRIPTION OF THE INVENTION

Figure 1:
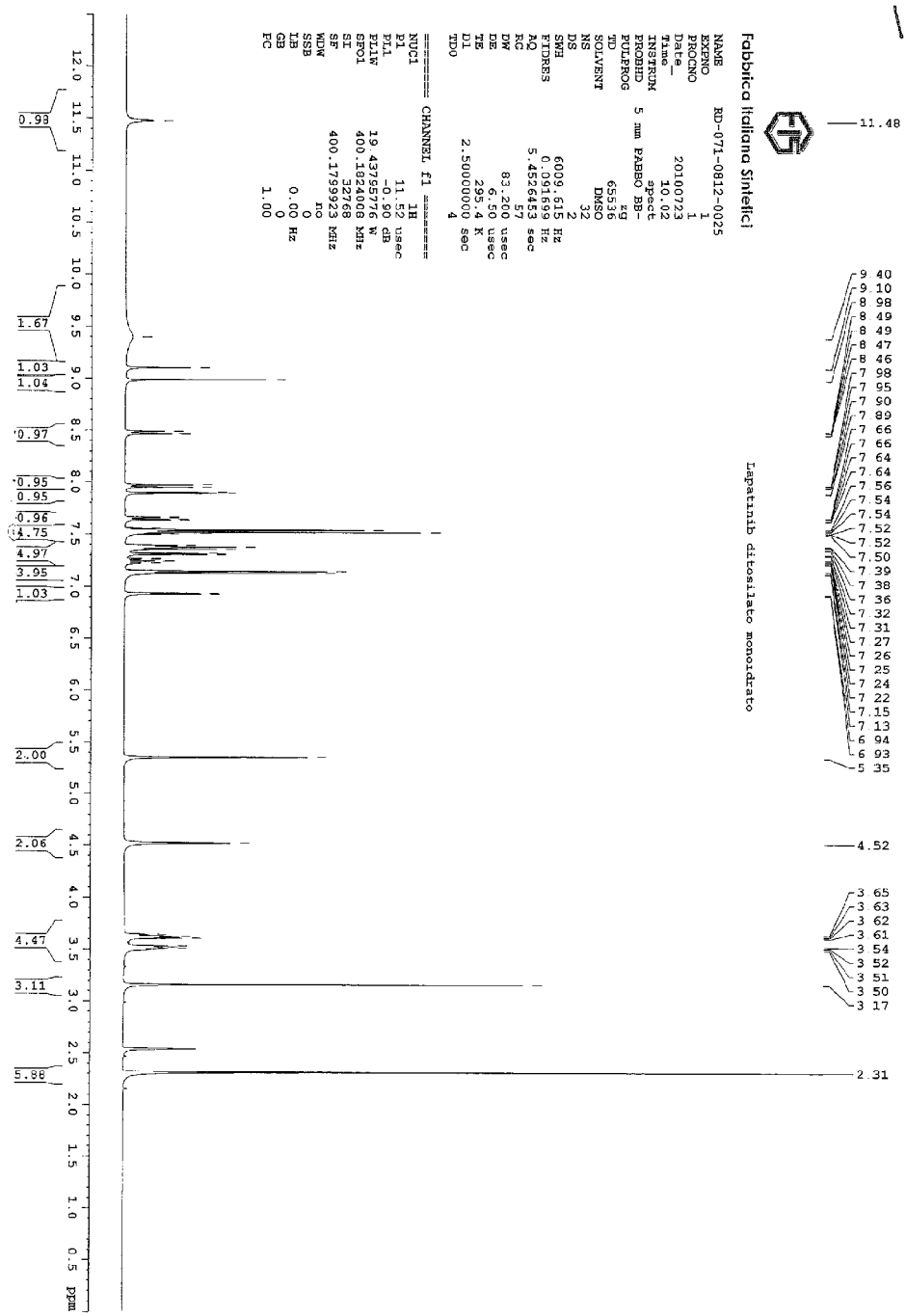
FIG. 1 shows the 1H-NMR spectrum of Lapatinib monohydrate ditosylate obtained according to a method of the present invention.

The present invention relates to N-{3-chloro-4-[(2-fluorobenzyl)oxy]phenyl}-6-[5-({[2-(methylsulfonyl)ethyl]amino}methyl)furan-2-yl] quinazoline-4-amine compound of formula (I) or a salt thereof:

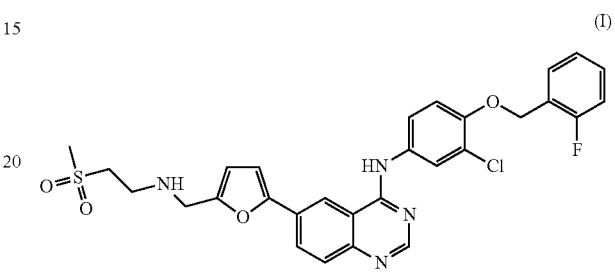

(I)

preferably in form of a ditosylate salt or as a monohydrate ditosylate salt of formula (I-bis):

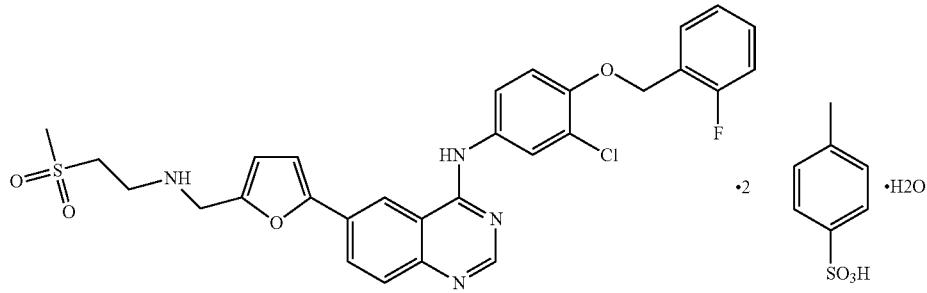

(I-bis)

possibly also comprising 0.01 to 5.0 percent area (HPLC) of Lapatinib or a salt thereof or compound of formula (I) or a salt thereof having at least a 95.0 HPLC purity (area percent).

The compound of formula (I) is both an impurity of Lapatinib and a precursor of a genotoxic impurity of Lapatinib.

The following degradation/hydrolysis mechanism was surprisingly discovered:

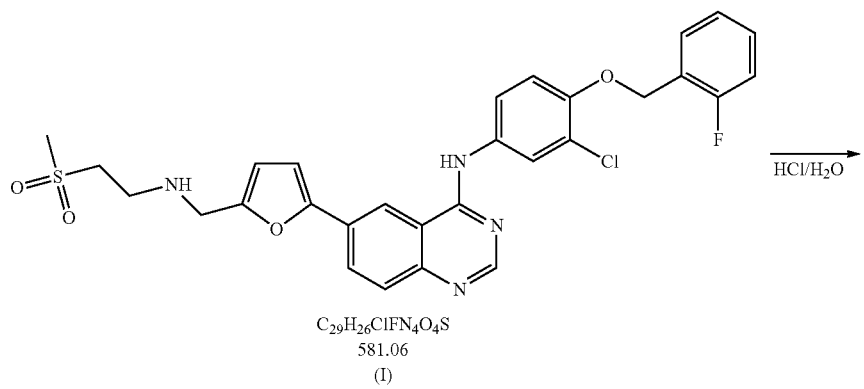

C29H26ClFN4O4S
581.06
(I)

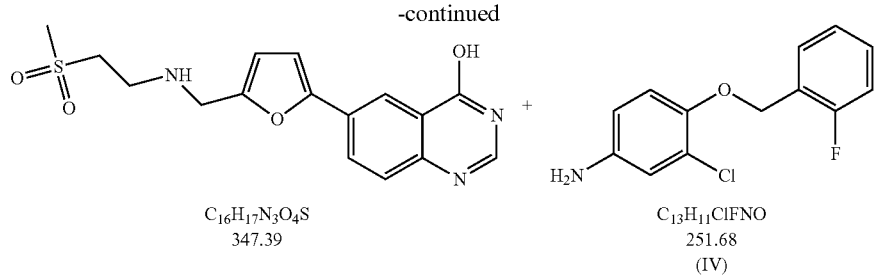

C₁₆H₁₇N₃O₄S
347.39

C₁₃H₁₁ClFNO
251.68
(IV)

This process results in the formation of significant amounts of 3-chloro-4-[(2-fluorobenzyl)oxy]aniline of formula (IV):

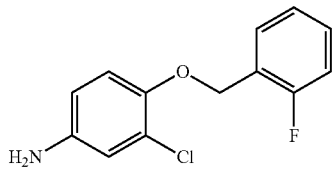

(IV)

a substance which, as the aniline parent, is genotoxic. Indeed, an analogous compound with fluorine in the meta position instead of in the ortho position is classified as a Mutagen of category 3, with R68 risk phrase, in the ESIS database of the European Commission.

Thus, it is important to reduce as much as possible the amount of the compound of formula (I), impurity of Lapatinib and precursor of genotoxic impurity of the Lapatinib, in Lapatinib or salts thereof. For such purpose, Lapatinib or salts thereof comprising less than 0.05 percent area (HPLC) of this impurity insure the quality of the drug product.

During the development of the process of synthesis of Lapatinib monohydrate ditosylate neither this impurity nor its synthetic precursors were observed because of the structural similarity the impurity has with the active ingredient. Indeed, the impurity eluge together with the active ingredient and thus the signal thereof was covered by that of Lapatinib.

Furthermore, it was surprisingly discovered that this impurity of Lapatinib and all the synthetic precursors thereof behave, in terms of solubility and reactivity, very similarly to Lapatinib and the synthetic precursors thereof. Thus the impurity in the 3-chloro-4-[(2-fluorobenzyl)oxy]aniline of formula (IV) raw material:

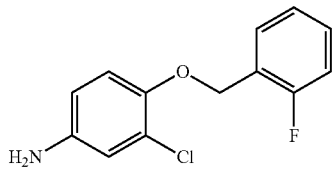

(IV)

is retained during the entire synthesis process of Lapatinib monohydrate ditosylate.

The present invention addresses these problems by providing Lapatinib or a salt thereof comprising an amount of impurity of formula (I) or a salt thereof lower than about 0.05 percent area by means of HPLC chromatographic analysis or lower than about 0.05 w/w %. In certain embodiments Lapatinib is in the form of Lapatinib monohydrate ditosylate.

In order to reduce the amount of an impurity in an active ingredient it is, of course, necessary to detect the presence thereof using appropriate analytical methods. Only after identifying and quantifying an impurity can one provide a method of synthesis capable of preventing the formation and/or provide for the removal thereof. For this purpose a reference standard or reference marker of this impurity is needed. The compound of formula (I) can be conveniently prepared using the following steps:

A) reacting 3-chloro-4-[(2-fluorobenzyl)oxy]aniline of formula (IV):

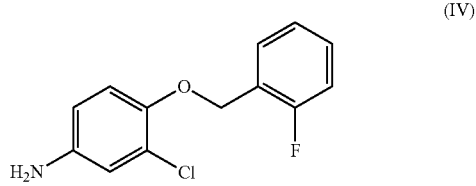 [SMILES: Nc1ccc(OCc2ccccc2F)c(Cl)c1]

(IV)

with 4-chloro-6-iodoquinazoline of formula (VIII):

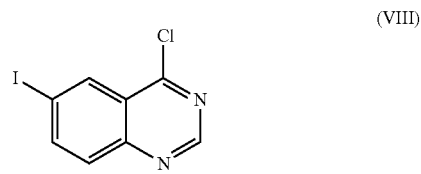 [SMILES: Clc1ncnc2ccc(I)cc12]

(VIII)

to yield N-{3-chloro-4-[(2-fluorobenzyl)oxy]phenyl}-6-iodoquinazoline-4-amine hydrochloride of formula (III):

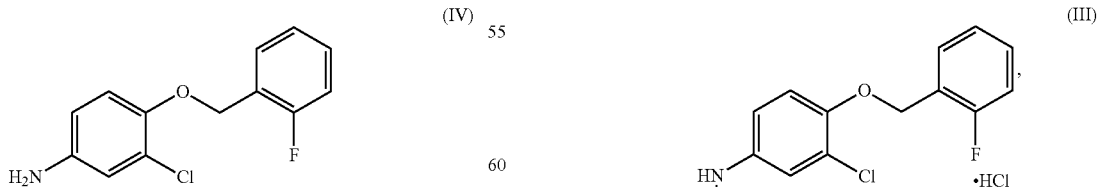

(III)

B) reacting the compound of formula (III) with the 2-formyl furan-5-boronic acid of formula (IX):

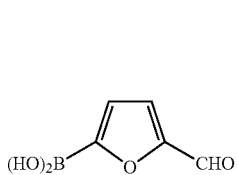

to yield 5-[4-({3-chloro-4-[(2-fluorobenzyl)oxy]phenyl}amino)quinazoline-6-yl]furan-2-carbaldehyde of formula (II):

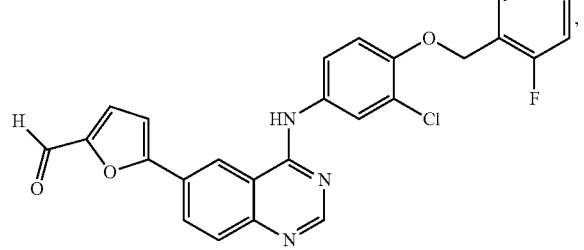

C) reacting the compound of formula (II) with 2-(methylsulfonyl)ethanamine hydrochloride to yield the compound of formula (I);

D) optionally the compound of formula (I) may be converted into a ditosylate salt or a monohydrate ditosylate salt.

In certain embodiments in step (b) the filtration of the inorganic salts present in the reaction mixture are carried out at a temperature between about 50° C. and about 60° C. to provide a higher yield compared to lower temperatures.

The N-{3-chloro-4-[(2-fluorobenzyl)oxy]phenyl}-6-iodoquinazoline-4-amine hydrochloride compound of formula (III):

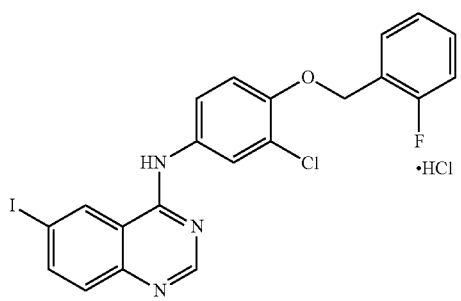

also may be obtained in a free base form. The 5-[4-({3-chloro-4-[(2-fluorobenzyl)oxy]phenyl}amino)quinazoline-6-yl]furan-2-carbaldehyde compound of formula (II):

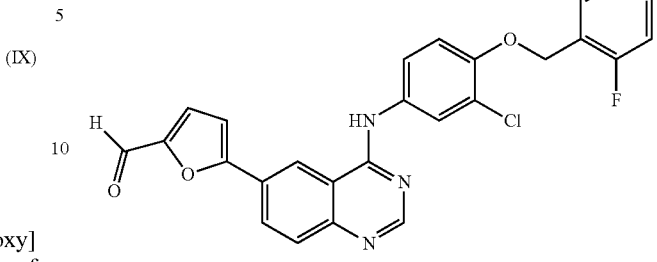

vice versa, also may be obtained in the form of a salt, for example hydrochloride.

Once prepared, the compound of formula (I) according to methods of the present invention also may be conveniently used in a method for the identification of the compound of formula (I) in Lapatinib or a salt thereof as follows:

a) adding a known amount of compound of formula (I) or a salt thereof to a Lapatinib sample or a salt thereof, b) carrying out HPLC analysis of the Lapatinib sample or a salt thereof of step a), c) detecting the HPLC peak of the compound of formula (I);

or by means of the following method:

a1) analysing the compound of formula (I) or a salt thereof by means of HPLC, b1) analysing the Lapatinib sample or a salt thereof by means of HPLC, c1) detecting the HPLC peak of the compound of formula (I) by comparing the retention times or relative retention times.

Methods according to certain embodiments of the present invention allow identification of the peak in the chromatogram of Lapatinib or a salt thereof regarding the impurity compound of formula (I). The analysis may be of the HPLC and GC type.

In addition, the impurity peak in Lapatinib or a salt thereof for the compound of formula (I), also may be quantified by means of the following method:

i) measuring the peak area corresponding to the compound of formula (I) in a Lapatinib sample or a salt thereof having an unknown amount of this compound by means of HPLC;

ii) measuring the peak area corresponding to a reference standard containing a known amount of compound of formula (I) or a salt thereof by means of HPLC, iii) defining the amount of compound of formula (I) in Lapatinib or a salt thereof by comparing the area measured in step a) with that measured in step b).

Thus, the compound of formula (I) or a salt thereof may be used as a reference marker or reference standard respectively for the identification and/or the quantification of the same in Lapatinib or a salt thereof.

Such methods allow for the preparation of Lapatinib or a salt thereof, preferably monohydrate ditosylate, having an amount of impurity of formula (I) or a salt thereof lower than about 0.05 percent area by means of chromatographic analysis or lower than about 0.05 percent weight on weight, having the following steps:

1) providing 3-chloro-4-[(3-fluorobenzyl)oxy]aniline of formula (X):

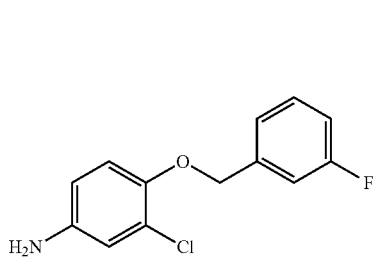

wherein it comprises less than about 0.15 percent area by means of chromatographic analysis or lower than about 0.15 percent weight on weight of 3-chloro-4-[(2-fluorobenzyl) oxy]aniline of formula (IV):

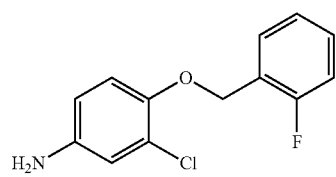

2) reacting 3-chloro-4-[(3-fluorobenzyl)oxy]aniline of formula (X) with 4-chloro-6-iodoquinazoline of formula (VIII):

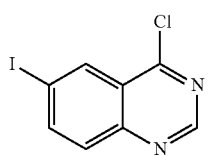

to yield N-{3-chloro-4-[(3-fluorobenzyl)oxy]phenyl}-6-iodoquinazoline-4-amine hydrochloride of formula (XI):

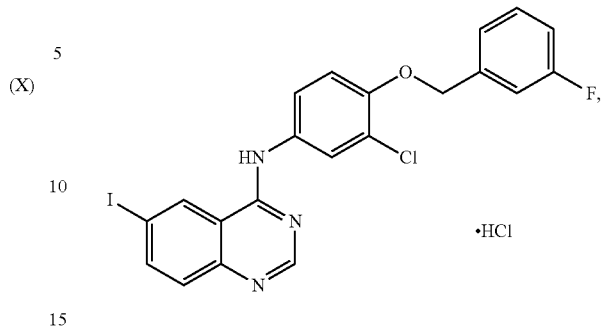

3) reacting the compound of formula (XI) with the 2-formyl furan-5-boronic acid of formula (IX):

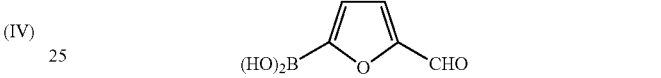

to yield 5-[4-({3-chloro-4-[(3-fluorobenzyl)oxy]phenyl}amino)quinazoline-6-yl]furan-2-carbaldehyde of formula (XII):

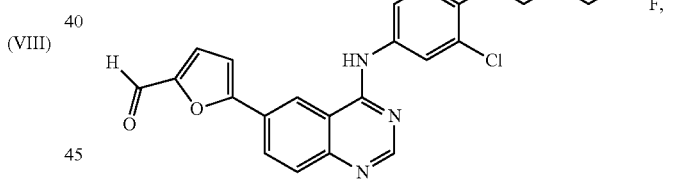

4) reacting the compound of formula (XII) with 2-(methylsulfonyl)ethanamine hydrochloride to yield Lapatinib of formula (XIII):

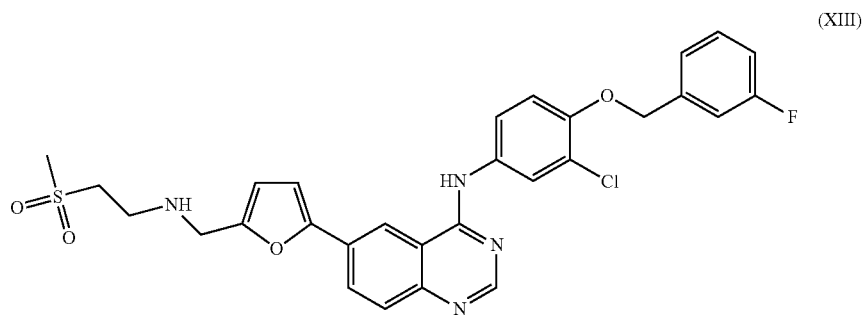 [SMILES: CS(=O)(=O)CCNCc1ccc(-c2ccc3ncnc(Nc4ccc(OCc5cccc(F)c5)c(Cl)c4)c3c2)o1]

5) optionally the Lapatinib of formula (XIII) may be converted into a ditosylate salt or a monohydrate ditosylate salt.

The experimental methods (see Example 8) for preparing Lapatinib and Lapatinib monohydrate ditosylate according to methods described above are identical to those indicated in Examples 3-7 with the sole difference being the use of—in example 3-3-chloro-4-[(3-fluorobenzyl)oxy]aniline of formula (X) instead of 3-chloro-4-[(2-fluorobenzyl)oxy] aniline of formula (IV) and continued synthesis with the corresponding intermediates.

Lapatinib monohydrate ditosylate whose 1H-NMR spectrum is indicated in FIG. 1 may be obtained.

Thus, the use of 3-chloro-4-[(3-fluorobenzyl)oxy]aniline of formula (X):

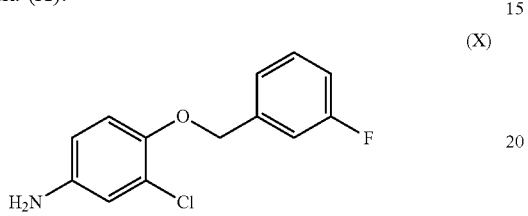

(X)

comprising less than 0.15 percent area by means of chromatographic analysis or lower than about 0.15 percent weight on weight of 3-chloro-4-[(2-fluorobenzyl)oxy]aniline of formula (IV):

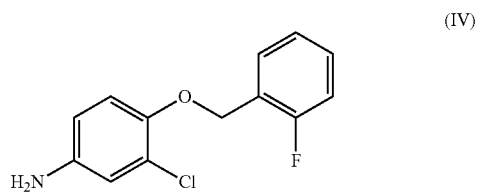 [SMILES: Nc1ccc(OCc2ccccc2F)c(Cl)c1]

(IV)

is thus useful for preparing Lapatinib or a salt thereof with the aforementioned amounts of compound (I) or a salt thereof.

Lapatinib or a salt thereof comprising less than about 0.05 percent area by means of chromatographic analysis or lower than about 0.05 percent weight on weight of compound of formula (I) or a salt thereof, obtainable through methods according to the present invention, can be used for preparing pharmaceutical compositions having one or more pharmacologically acceptable carriers. Such compositions may be used in the treatment of advanced metastatic lung cancer.

EXAMPLES

Example 1

Preparation of 2-chloro-[(2-fluorobenzyl)oxy]-4-nitrobenzene of formula (V)

Synthesis Scheme

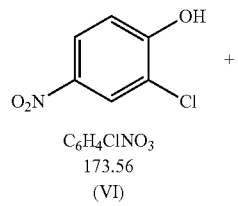

C₆H₄ClNO₃
173.56
(VI)

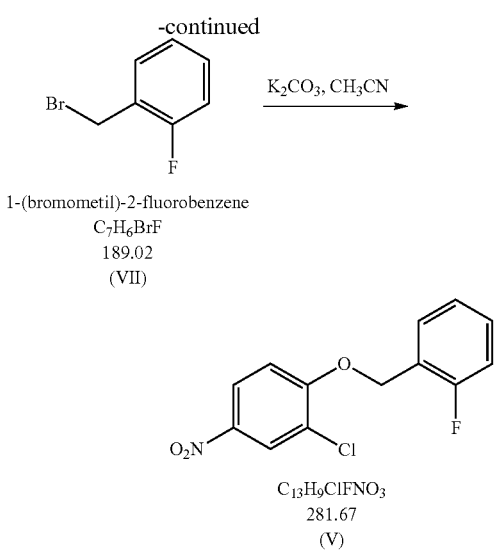

1-(bromometil)-2-fluorobenzene
C₇H₆BrF
189.02
(VII)

C₁₃H₉ClFNO₃
281.67
(V)

1-(bromomethyl)-2-fluorobenzene

In a glass flask provided with a condenser, thermometer, mechanical stirrer and nitrogen inlet, —under nitrogen flow—22.9 g of 2-Chloro-4-nitrophenol of formula (VI), 25.0 g of 1-(bromomethyl)-2-fluorobenzene of formula (VII) and 230 mL of Acetonitrile were introduced. Stirring was carried out at 20-25° C. and 20.1 g of potassium carbonate were added. The mixture was stirred at 60° C. for 2 hours. Upon completing the reaction cooling was carried out and the reaction mixture was poured into 230 mL of purified water pre-cooled at 0-5° C. The precipitation of a yellowish solid was observed. The formed solid was filtered thoroughly draining the mother liquors and washing with 2×46 mL of water/acetonitrile 1:1 mixture pre-cooled at 0-5° C. Washing was then carried out with 46 mL of n-Hexane pre-cooled at 0-5° C. The product was dried in an oven under vacuum for 4-5 hours at 45° C. 33.9 g of product as an almost white solid equivalent to a 91.2% yield were obtained.

Example 2

Preparation of 3-chloro-4-[(2-fluorobenzyl)oxy]aniline of formula (IV)

Synthesis Scheme

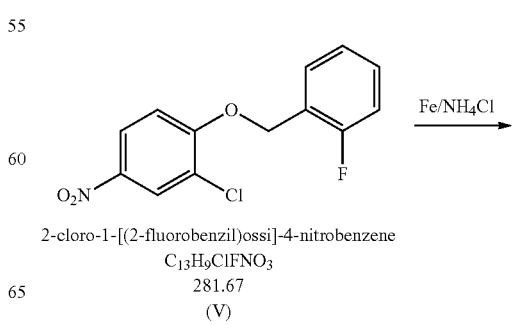

2-cloro-1-[(2-fluorobenzil)ossi]-4-nitrobenzene
C₁₃H₉ClFNO₃
281.67
(V)

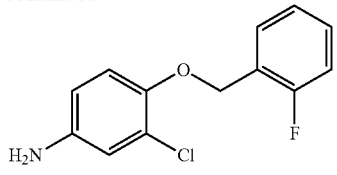

3-cloro-4-[(2-fluorobenzil)ossi]anilina
C₁₃H₁₁ClFNO
251.68
(IV)

2-Chloro-[(2-fluorobenzyl)oxy]-4-nitrobenzene 3-chloro-4-[(2-fluorobenzyl) oxy]aniline In a glass flask provided with a condenser, thermometer, mechanical stirrer and nitrogen inlet, —under nitrogen flow—25.0 g of 2-Chloro-[(2-fluorobenzyl)oxy]-4-nitrobenzene of formula (V), 14.9 g of powder iron (MW: 55.85, 3.0 mol. equiv.), 42.7 g of ammonium chloride (MW: 53.49, 9.0 mol. equiv.), 350 mL of Ethanol denatured with Methanol and 85 mL of purified water were introduced. The reaction mixture was stirred at reflux temperature (68° C.) for 2 hours.

Figure 6:
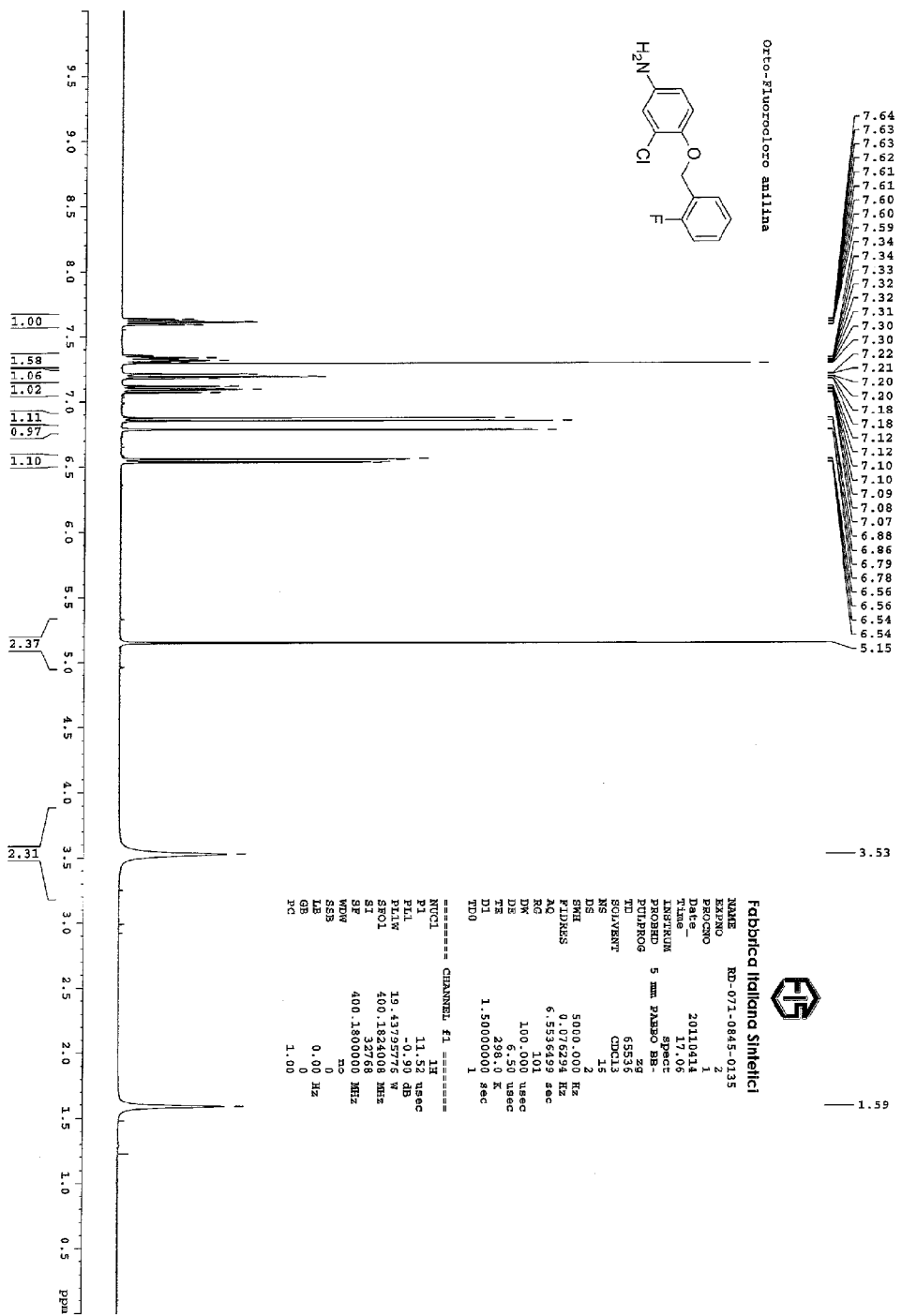
FIG. 6 shows the 1H-NMR spectrum of 3-chloro-4-[(2-fluorobenzyl)oxy]aniline of formula (IV)

Upon completing the reaction, cooling was carried out at 20-25° C. The insoluble iron oxides were filtered on dicalite and the filtrate was evaporated to residue at an external temperature of 40-45° C. 275 mL of dichloromethane were added. The suspension was filtered on paper to remove the inorganic salts. Water residue was separated. The organic phase was anhydrified on anhydrous sodium sulphate, filtered and concentrated to residue eliminating the solvent thoroughly. 19.1 g of product were obtained as a pale yellow solid equivalent to an 85.5% molar yield. 1H-NMR spectrum according to FIG. 6.

Example 3

Preparation of N-{3-chloro-4-[(2-fluorobenzyl)oxy]phenyl}-6-iodoquinazoline-4-amine hydrochloride of formula (III)

Synthesis Scheme

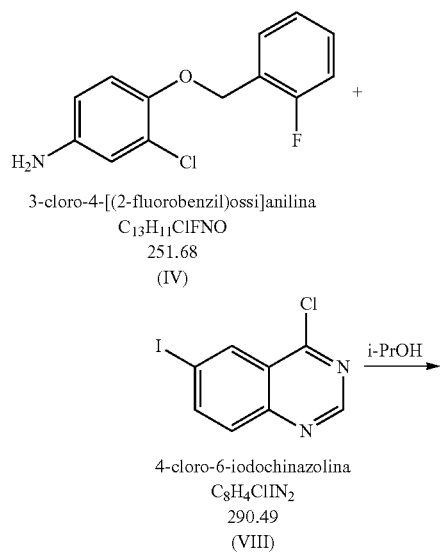

3-cloro-4-[(2-fluorobenzil)ossi]anilina
C₁₃H₁₁ClFNO
251.68
(IV)

4-cloro-6-iodochinazolina
C₈H₄ClIN₂
290.49
(VIII)

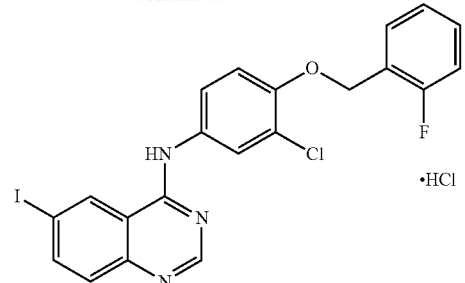

N-{3-cloro-4-[(2-fluorobenzil)ossi]fenil}-6-iodochinazolin-4-ammina cloridrato
C₂₁H₁₄ClFIN₃O·ClH
542.16
(III)

3-chloro-4-[(2-fluorobenzyl)oxy] aniline 4-chloro-6-iodoquinazoline

Figure 5:
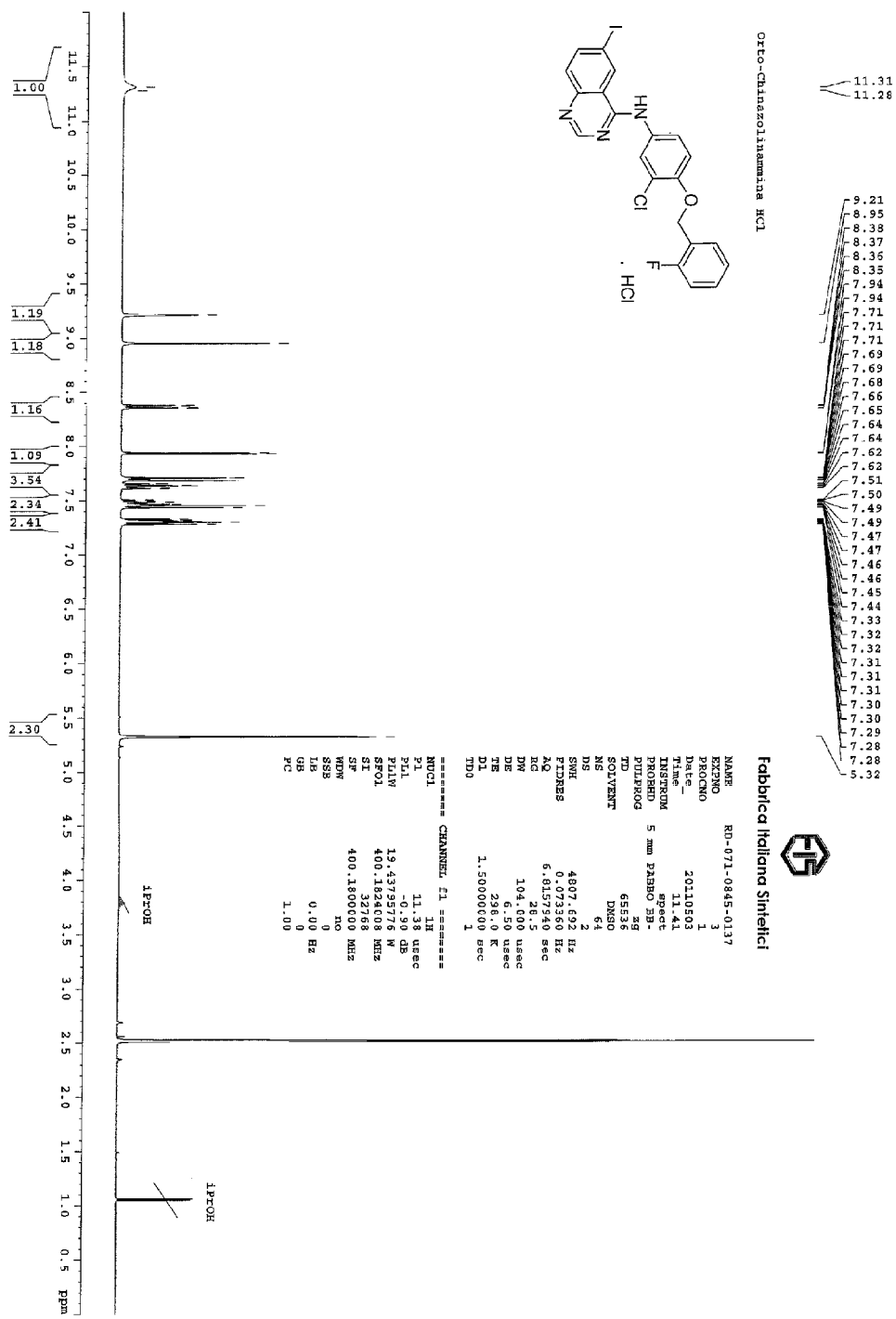
FIG. 5 shows the 1H-NMR spectrum of N-{3-chloro-4-[(2-fluorobenzyl)oxy]phenyl}-6-iodoquinazoline-4-amine hydrochloride of formula (III)

N-(3-chloro-4-[(2-fluorobenzyl)oxy]phenyl)-6-iodo-quinazoline-4-amine hydrochloride In a glass flask provided with a condenser, thermometer, mechanical stirrer and nitrogen inlet, —under nitrogen flow—15.0 g of 3-chloro-4-[(2-fluorobenzyl)oxy]aniline of formula (IV), 17.49 g of 4-chloro-6-iodoquinazoline of formula (VIII)(available in the market), 300 mL of Isopropanol were introduced. The reaction mixture was stirred at 70° C. for 2 hrs. Upon completing the reaction cooling was carried out at ambient temperature. The formed yellow solid was filtered washing the solid with 20 mL of cold Isopropanol. 31.9 g of product equivalent to a 98.7% molar yield were obtained. 1H-NMR spectrum according to FIG. 5.

Example 4

Preparation of 5-[4-({3-chloro-4-[(2-fluorobenzyl)oxy]phenyl}amino)quinazoline-6-yl]furan-2-carbaldehyde of formula (II)

Synthesis Scheme

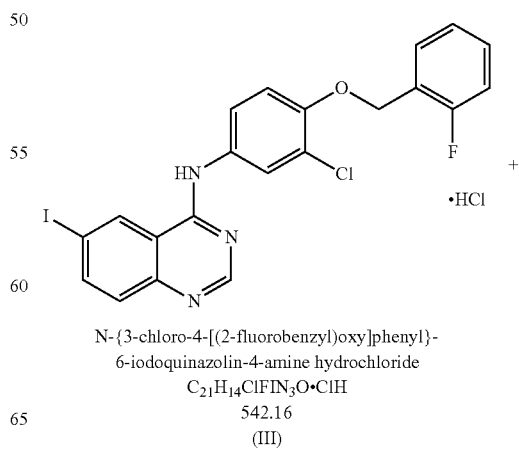

N-{3-cloro-4-[(2-fluorobenzil)oxy]phenyl}-6-iodoquinazolin-4-amine hydrochloride
C₂₁H₁₄ClFIN₃O·ClH
542.16
(III)

-continued

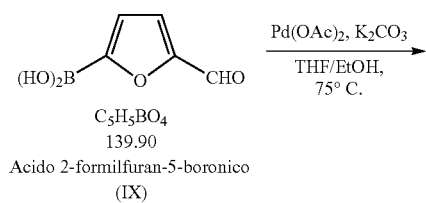

C$_5$H$_5$BO$_4$
139.90
Acido 2-formilfuran-5-boronico
(IX)

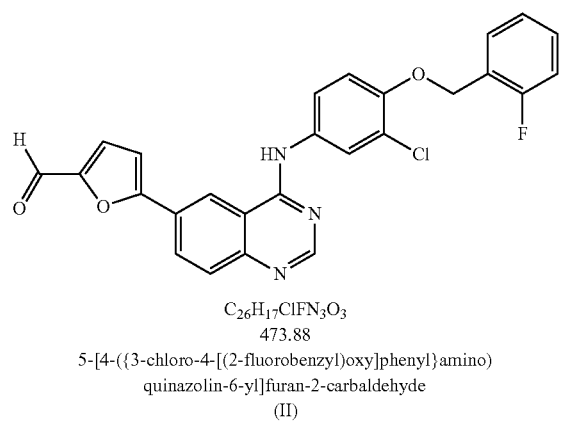

C$_{26}$H$_{17}$ClFN$_3$O$_3$
473.88
5-[4-({3-chloro-4-[(2-fluorobenzyl)oxy]phenyl}amino)quinazolin-6-yl]furan-2-carbaldehyde
(II)

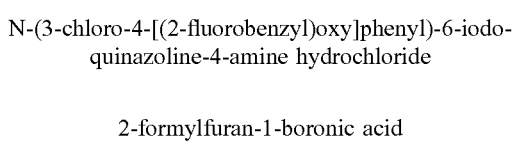

N-(3-chloro-4-[(2-fluorobenzyl)oxy]phenyl)-6-iodo-quinazoline-4-amine hydrochloride 2-formylfuran-1-boronic acid

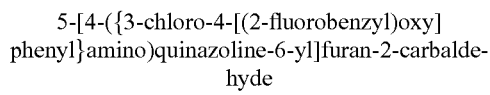

5-[4-({3-chloro-4-[(2-fluorobenzyl)oxy]phenyl}amino)quinazoline-6-yl]furan-2-carbaldehyde In a glass flask provided with a condenser, thermometer, mechanical stirrer and nitrogen inlet, —under nitrogen flow—25.0 g of N-{3-chloro-4-[(2-fluorobenzyl)oxy]phenyl}-6-iodoquinazoline-4-amine hydrochloride of formula (III), 7.26 g of 2-formyl furan-5-boronic acid of formula (IX) (1.126 mol. equiv.), 0.31 g of Palladium acetate, 19.4 g of Potassium carbonate, 190 mL of absolute ethanol and 190 mL of THF were introduced.

Figure 4:
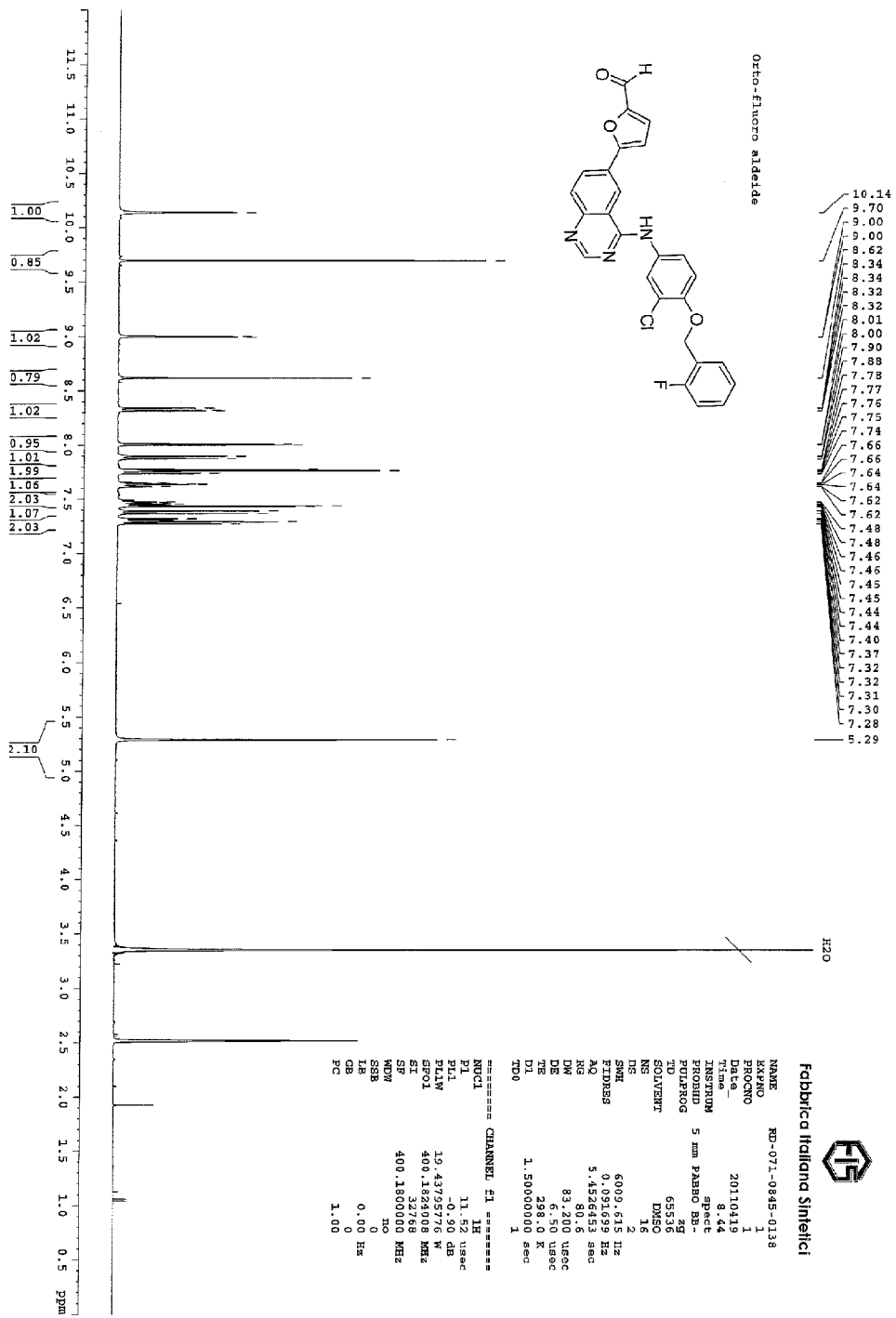
FIG. 4 shows the 1H-NMR spectrum of 5-[4-({3-chloro-4-[(2-fluorobenzyl)oxy]phenyl}amino)quinazoline-6-yl]furan-2-carbaldehyde of formula (II)

The reaction mixture was heated at T=75° C. for 1 hr. Upon completing the reaction cooling was carried out at 50-60° C. and 190 mL of Absolute ethanol and 190 mL of THF were added. Stirring was carried out at 50-60° C. for 1 hr then filtration was carried out at this temperature washing with 25 mL of Absolute ethanol and 25 mL of THF preheated at 50-60° C. 750 mL of purified water were added to the filtrate in one hour. Stirring was carried out at ambient temperature for 1.5 hours then filtration was carried out washing with 25 mL of Absolute ethanol. The product was dried under vacuum at 50° C. for 7-8 hours. 21.6 g of product equivalent to a 98.8% molar yield were obtained. 1H-NMR spectrum according to FIG. 4.

Example 5

Preparation of N-{3-chloro-4-[(2-fluorobenzyl)oxy]phenyl}-6-[5-({[2-(methylsulfonyl)ethyl]amino}methyl)furan-2-yl]quinazoline-4-amine of formula (I)

Synthesis Scheme

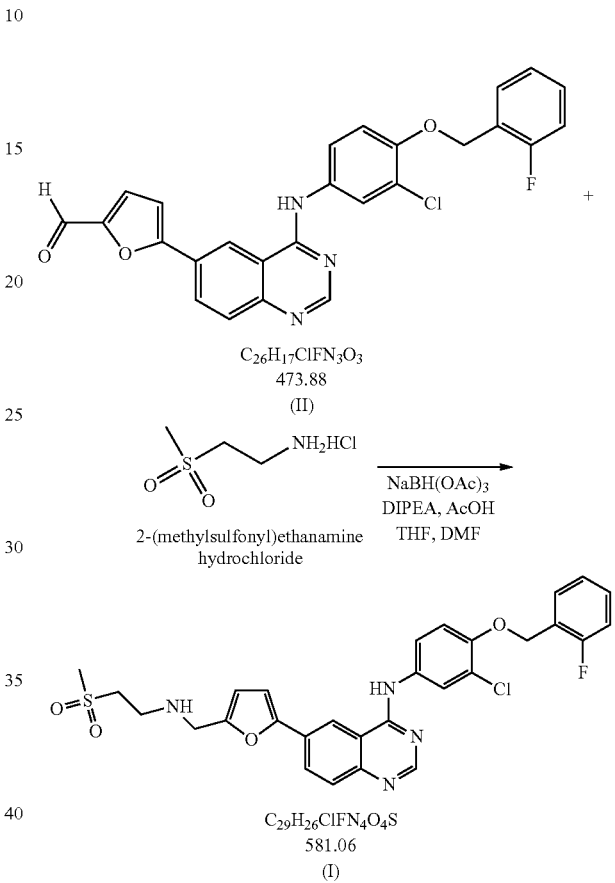

2-(methylsulfonyl)ethanamine hydrochloride

In a 4-neck glass flask provided with mechanical stirrer, condenser and thermometer, —under nitrogen—15.0 g of 5-[4-({3-chloro-4-[(2-fluorobenzyl)oxy]phenyl}amino)quinazoline-6-yl]furan-2-carbaldehyde of formula (II), 8.18 g of 2-(methylsulfonyl)ethanamine hydrochloride (1.64 mol. equiv.), 75 mL of THF, 15 mL of DMF, 7.22 mL of Glacial acetic acid (4 mol. equiv.) and 22.05 mL of Diisopropylamine (DIPEA) (4 mol. equiv.) were introduced. Stirring was carried out at 35° C. for 1 hour and the cooling was carried out at 20-25° C. and 16.77 g of Sodium triacetoxyborohydride (2.5 mol. equiv.) are added. Stirring was carried out at 25° C. for 2 hours. Upon completing the reaction 225 mL of ethyl acetate were added and 45 mL of purified water were dripped in 30 minutes under stirring. 15.0 mL of 30% NaOH solution (w/w) were subsequently dripped in 30 minutes up to a pH of about 11-11.5. The phases were separated and the organic phase was washed with 2×75 mL of 25% w/w solution of Ammonium chloride and 2×45 mL of purified water. The organic phase was concentrated under vacuum up to residue.

Figure 3:
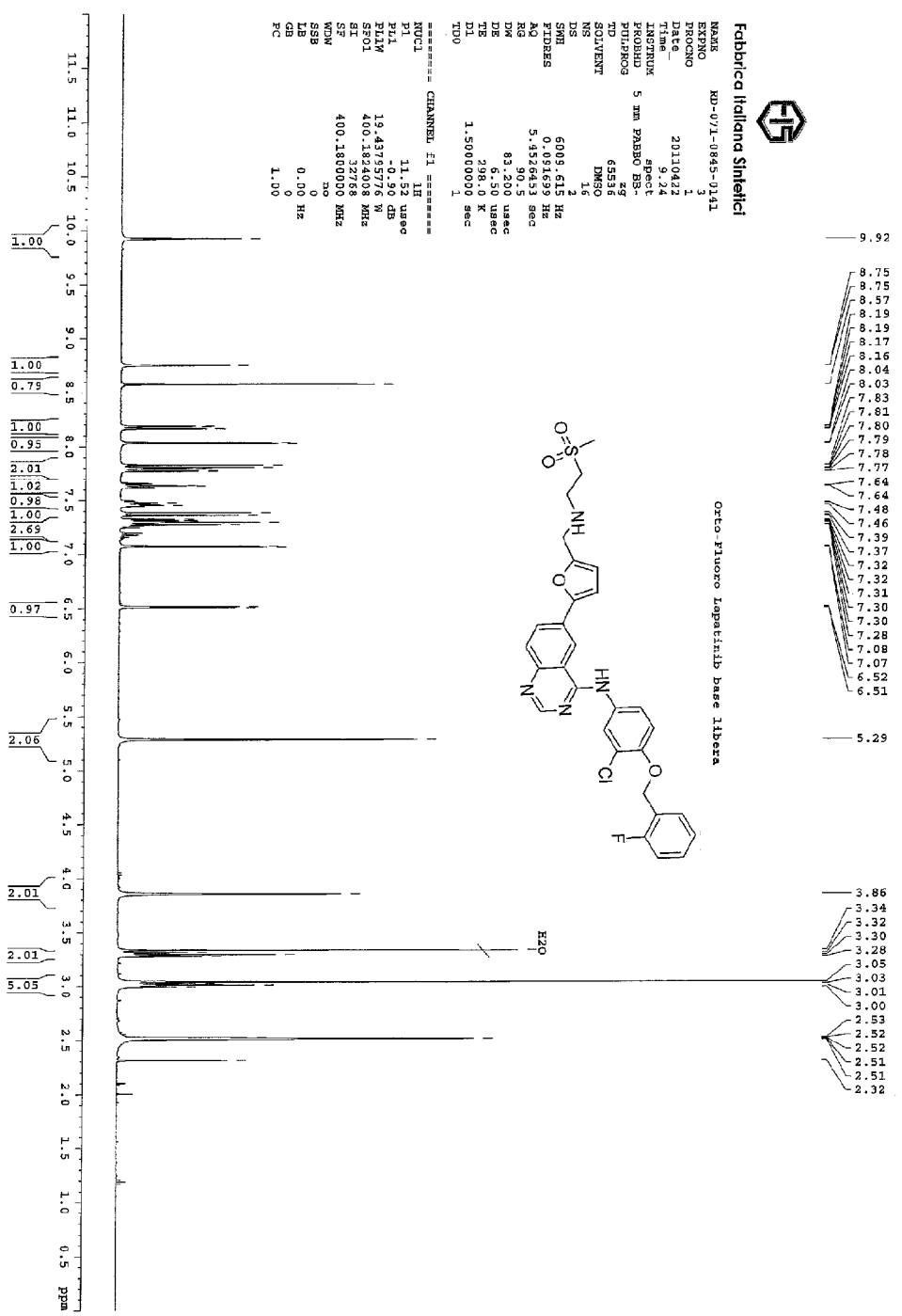
FIG. 3 shows the 1H-NMR spectrum of the N-{3-chloro-4-[(2-fluorobenzyl)oxy]phenyl}-6-[5-({[2-(methylsulfonyl)ethyl]amino} methyl)furan-2-yl]quinazoline-4-amine compound of formula (I), as a free base.

A small amount of the obtained solid equivalent to 1.0 g was taken and triturated for 1 hour in 5 mL of ethyl acetate. Filtration was carried out and the solid was washed using 2 mL of ethyl acetate and dried. 0.7 g of product were thus obtained. 1H-NMR spectrum according to FIG. 3.

Example 6

Preparation of N-{3-chloro-4-[(2-fluorobenzyl)oxy]phenyl}-6-[5-({[2-(methylsulfonyl)ethyl]amino}methyl)furan-2-yl] quinazoline-4-amine ditosylate salt of formula (I)

Synthesis Scheme

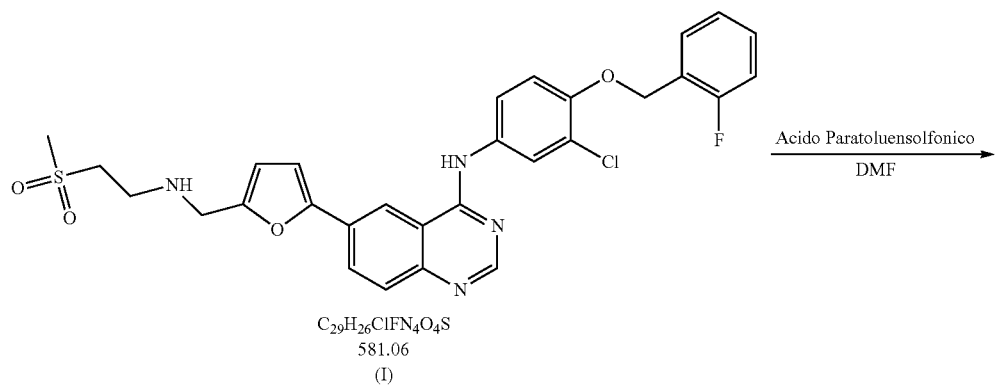

Paratoluenesulfonic Acid

Figure 2:
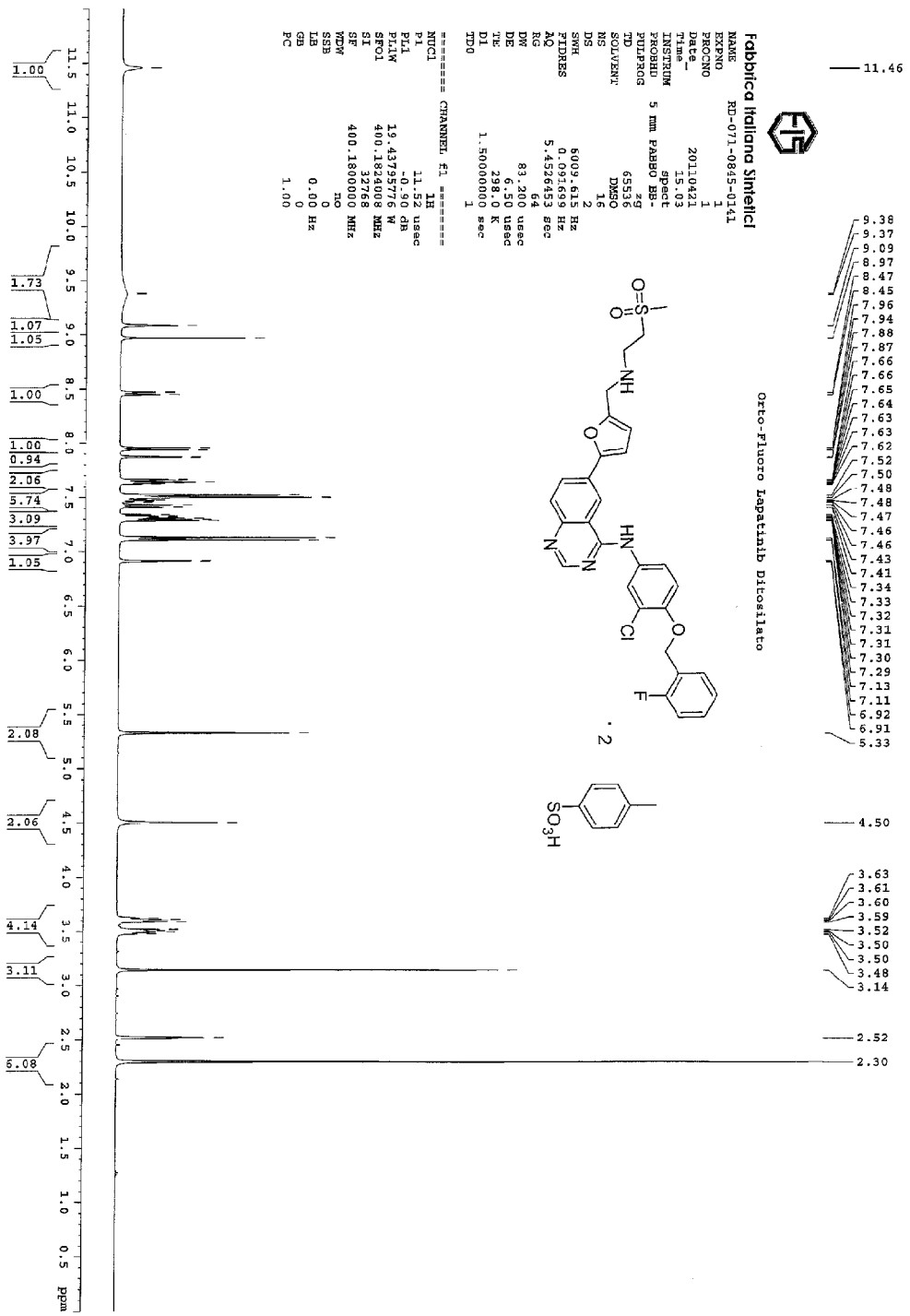
FIG. 2 shows the 1H-NMR spectrum of the N-{3-chloro-4-[(2-fluorobenzyl)oxy]phenyl}-6-[5-({[2-(methylsulfonyl)ethyl]amino}methyl)furan-2-yl]quinazoline-4-amine compound of formula (I) as a ditosylate salt.

The residue obtained from the concentration of the organic phase in Example 5 constituted by the compound of formula (I) (as a free base) was recovered using 52.5 mL of dimethylformamide. Heating was carried out at 40° C. for 15 minutes and filtration was carried out on a dicalite panel. The panel was washed using 39.5 ml of dimethylformamide pre-heated at 50° C. The organic phases were combined. They were brought to 40° C. and 12.64 g of monohydrate Paratoluenesolfonic acid (2.1 mol. equiv.) were added to subsequent portions. Stirring was carried out at 40° C. for 1 hour and then cooling was carried out in 3-4 hours at 0° C. Stirring was carried out for 1 hour a 0° C., then cooling was carried out at −10° C. and then stirring was carried out for 1 hour. The suspension was filtered and the solid was washed using 9 mL of Dimethylformamide pre-cooled at −10° C. The solid was recovered using 75 mL of DMF and pulping was carried out at 40° C. for 2 hours. Cooling was carried out slowly at −10° C. and stirring was carried out at this temperature for 1-2 hours, the solid was filtered and washed using 9 ml of DMF pre-cooled at −10° C. The solid was dried in an oven under vacuum at 70° C. for at least 10 hours. 21.4 g of product equivalent to a 73.0%/molar yield were obtained. 1H-NMR spectrum according to FIG. 2.

Example 7

Preparation of N-{3-chloro-4-[(2-fluorobenzyl)oxy]phenyl}-6-[5-({[2-(methylsulfonyl)ethyl]amino}methyl)furan-2-yl] quinazoline-4-amine monohydrate ditosylate salt of formula (I-bis)

Synthesis Scheme

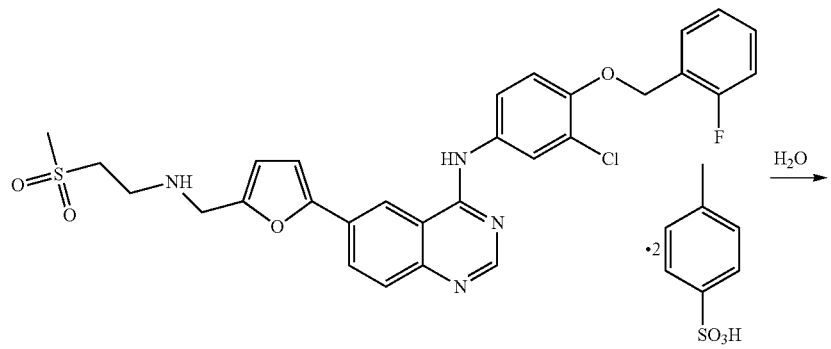

$C_{29}H_{26}ClFN_4O_4S \cdot 2\ C_7H_8O_3S$
925.45
(I)

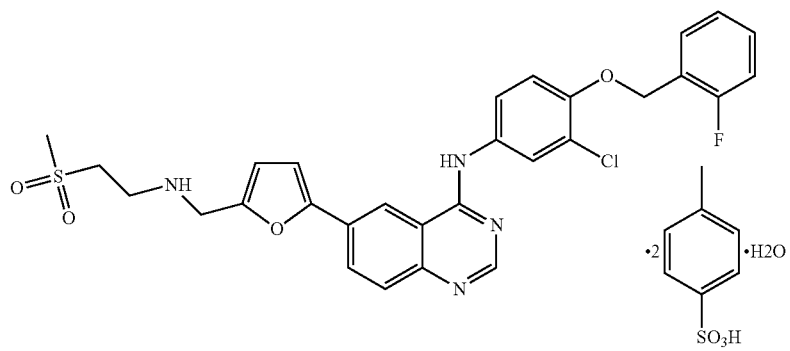

$C_{29}H_{26}ClFN_4O_4S \cdot 2\ C_7H_8O_3S \cdot H_2O$
943.47
(I-bis)

In a 4-neck glass flask provided with mechanical stirrer, condenser and thermometer,—under nitrogen—50.0 g of N-{3-chloro-4-[(2-fluorobenzyl)oxy]phenyl}-6-[5-({[2-(methylsulfonyl)ethyl]amino}methyl)furan-2-yl] quinazoline-4-amine of formula (I) ditosylate salt and 500 mL of water were introduced. Stirring was carried out for 36 hours at ambient temperature. Filtration was carried out thoroughly draining the product and the product was washed using the mother liquors. The product was dried at ambient temperature—under nitrogen flow—in a flask provided with a stirrer.

The product was thus dried for 24 hours at 55° C. up to K.F. around 1.94%. 50.5 g of product were obtained for a quantitative molar yield.

Example 8

Preparation of Lapatinib monohydrate ditosylate salt of formula (XIII-bis)

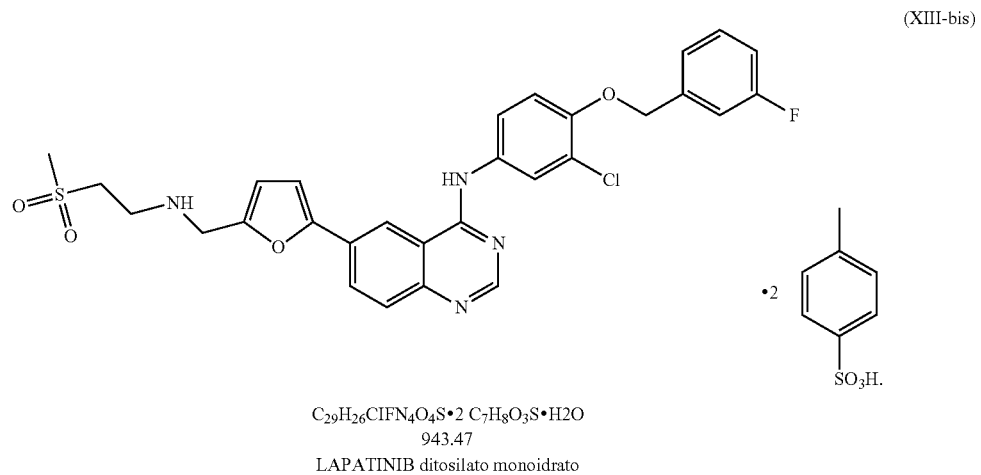 [SMILES: CS(=O)(=O)CCNCc1ccc(-c2ccc3ncnc(Nc4ccc(OCc5cccc(F)c5)c(Cl)c4)c3c2)o1 ; Cc1ccc(S(=O)(=O)O)cc1]

(XIII-bis)

$C_{29}H_{26}ClFN_4O_4S \cdot 2\ C_7H_8O_3S \cdot H_2O$
943.47
LAPATINIB ditosilato monoidrato

Lapatinib Monohydrate Ditosylate

The preparation of Lapatinib and Lapatinib monohydrate ditosylate was performed repeating the procedures of Examples 3-7 with the sole difference lying in the fact that in example 3 3-chloro-4-[(3-fluorobenzyl)oxy]aniline of formula (X) was used instead of 3-chloro-4-[(2-fluorobenzyl)oxy]aniline of formula (IV).

Figure 7:
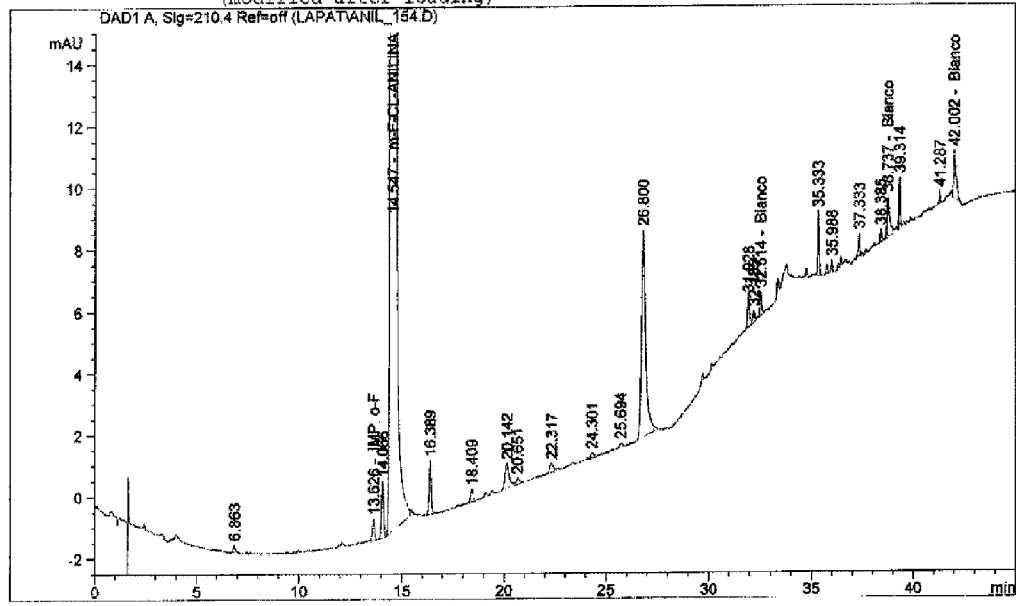
FIG. 7 shows the HPLC chromatogram of 3-chloro-4-[(3-fluorobenzyl)oxy]aniline of formula (X) containing 0.066 percent area (HPLC) of 3-chloro-4-[(2-fluorobenzyl)oxy] aniline impurity of formula (IV) used for preparing the Lapatinib monohydrate ditosylate of FIG. 8.
Figure 8:
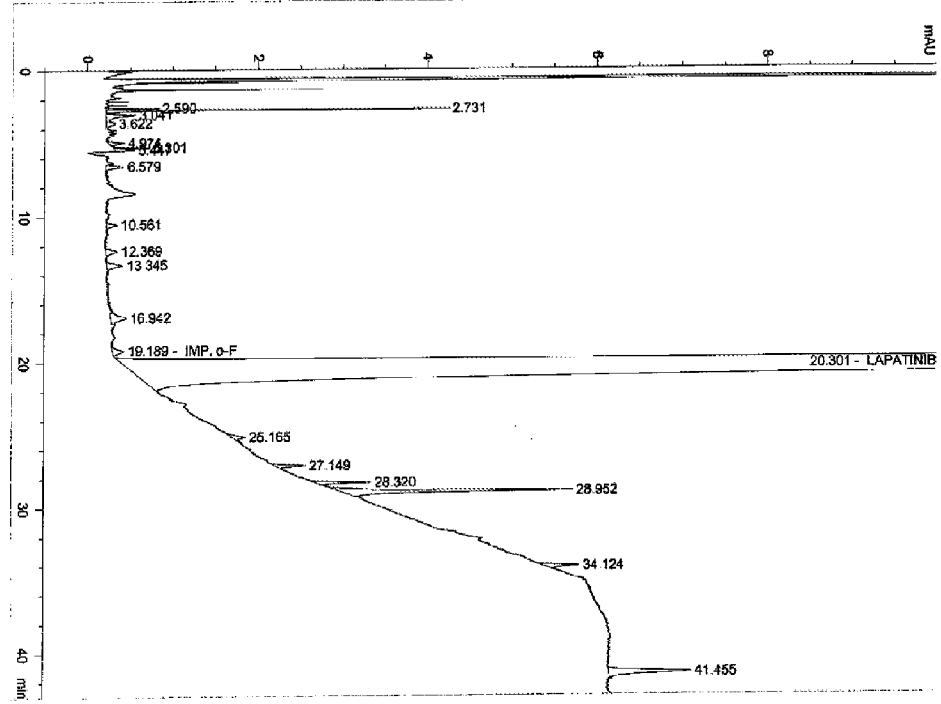
FIG. 8 shows the Lapatinib monohydrate ditosylate of formula (XIII-bis) containing 0.024 percent area (HPLC) of impurity of formula (I-bis) obtained according to the method of the invention.

In particular starting from a purchase batch of 3-chloro-4-[(3-fluorobenzyl)oxy]aniline of formula (X) containing 0.066 percent area (HPLC) of 3-chloro-4-[(2-fluorobenzyl)oxy]aniline impurity of formula (IV) (FIG. 7) Lapatinib monohydrate ditosylate of formula (XIII-bis) containing 0.024 percent area (HPLC) of impurity of formula (I-bis) was obtained through said method (FIG. 8).

FIG. 1 shows the 1H-NMR spectrum of the obtained Lapatinib monohydrate ditosylate and associated data.

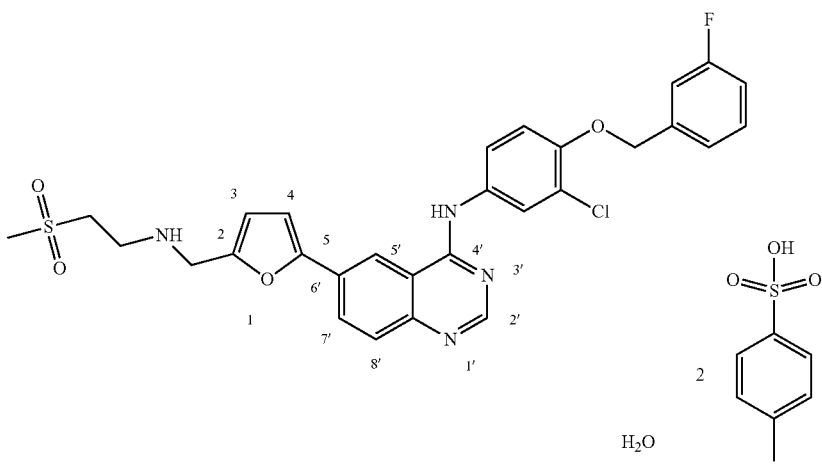 [SMILES: CS(=O)(=O)CCNCc1ccc(-c2ccc3ncnc(Nc4ccc(OCc5cccc(F)c5)c(Cl)c4)c3c2)o1 ; O ; Cc1ccc(S(=O)(=O)O)cc1]

1H NMR (400 MHz, DMSO-d6): δ 2.31 (s, 6H, CH3 (TsOH)); 3.17 (s, 3H, CH3S02); 3.50-3.65 (m, 4H, —S02CH2CH2NH—); 4.52 (s, 2, NH—CH2-furan); 5.35 (s, 2H, Ar0-CH2-Ar); 6.93 (d, J=3.4 Hz, 1H, CH (furan)); 7.14 (d, J=7.8 Hz, 4H, CH (TsOH)); 7.24 (dt, J=8.8, 2.1 Hz, 1H, Ar); 7.32 (d, J=3.4 Hz, 1H, CH (furan)); 7.53 (d, J=8.0 Hz, 4H, CH (TsOH)); 7.65 (dd, J=8.9, 2.5 Hz, Ar); 7.90 (d, J=2.6 Hz, 1H, H-5'); 7.97 (d, J=8.8 Hz, 1H, H-8'); 8.48 (dd, J=8.8, 1.5 Hz, 1H, H-T); 8.99 (s, 1H, H-2'); 9.10 (s, 1H, Ar); 9.40 (br. s, 1H, NH); 11.48 (s, 1H, NH).

Example 9

Analytic method for determining the amount of 3-chloro-4-[(2-fluorobenzyl)oxy]aniline impurity of formula (IV) in the 3-chloro-4-[(3-fluorobenzyl)oxy]aniline of formula (X)

Chromatography Conditions

| Column: | Waters Symmetry Shield 150 × 4.6 mm, 3.5 micron |
| --- | --- |
| Column temp: | 25° C. |
| Mobile phase A: | H3P04 0.1% |
| Mobile phase B: | Acetonitrile |
| Flow: | 1.2 mL/min. |

| Gradient: | | |
| --- | --- | --- |
| (minutes) | % A | % B |
| 0 | 85 | 15 |
| 15 | 70 | 30 |
| 20 | 66 | 34 |
| 26 | 60 | 40 |
| 40 | 0 | 100 |
| 44 | 0 | 100 |
| 45 | 85 | 15 |

| Detector: | UV at 210 nm |
| --- | --- |
| Post run: | 6 minutes |
| Injection volume: | 5 microL |
| Diluent: | H20/ACN (1/1) |

Applying the conditions described above the expected retention times were as indicated below (FIG. 7):

| Compound | RT (min) | RRT |
| --- | --- | --- |
| Impurity (IV) | 13.6 | 0.94 |
| Compound (X) | 14.5 | 1.00 |

The amount of impurity of formula (IV) was determined in percent area.

Example 10

Analytic method for determining the amount of impurity of formula (I-bis) in the Lapatinib monohydrate ditosylate of formula (XIII-bis)

Chromatography Conditions

| Analytic method obtained from WO 2010/017387 (TEVA) | |
| --- | --- |
| Column: | Zorbax SB Phenyl 100 × 4.6 mm, 1.8 micron or equivalent |
| Column temp: | 20° C. |
| Mobile phase A: | 80% (20 mM KH2P04 pH 5.0):20% Acetonitrile |
| Mobile phase B: | Acetonitrile |
| Flow: | 1.5 mL/min. |
| Detector: | UV at 210 nm |
| Post run: | 10 minutes |
| Injection volume: | 5 microL |
| Diluent: | H20/ACN (1/1) |

| Gradient: | | |
| --- | --- | --- |
| (minutes) | % A | % B |
| 0 | 70 | 30 |
| 20 | 70 | 30 |
| 34 | 35 | 65 |
| 42 | 35 | 65 |

Applying the conditions described above the expected retention times were as indicated below (FIG. 8):

| Compound | RT (min) | RRT |
| --- | --- | --- |
| o-F-Lapatinib | 19.2 | 0.95 |
| (LAP) Lapatinib | 20.3 | 1.00 |

The amount of impurity of formula (1-bis) was determined in percent area.

The identification and quantification of the content of formula (I) in Lapatinib allows for the production of the commercial product with very low levels of impurities.

The invention claimed is:

1. A method for detecting the compound of formula (I)

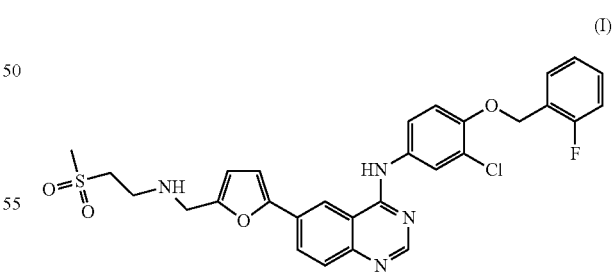

in Lapatinib or a salt thereof comprising:
a) adding a known amount of compound of formula (I) or a salt thereof to the Lapatinib sample or a salt thereof,
b) carrying out HPLC analysis of the Lapatinib sample or a salt thereof of step a), and
c) detecting the HPLC peak of the compound of formula (I).

2. A method for detecting the compound of formula (I)

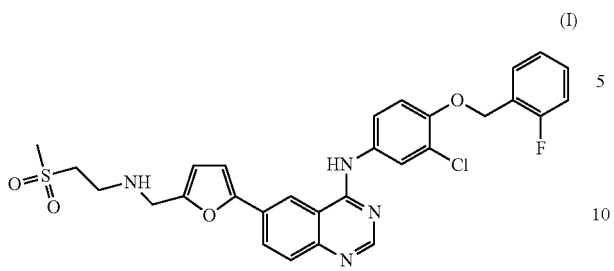

in Lapatinib or a salt thereof comprising:
a1) analysing the compound of formula (I) or a salt thereof by means of HPLC,
b1) analysing the Lapatinib sample or a salt thereof by means of HPLC, and
c1) detecting the HPLC peak of the compound of formula (I) by comparing the retention times or relative retention times.

3. A method for the quantification of the compound of formula (I)

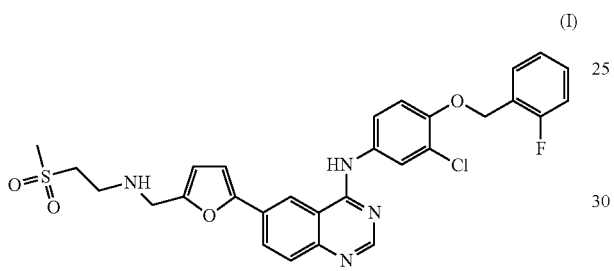

or a salt thereof in Lapatinib or a salt thereof comprising:
i) measuring the peak area corresponding to the compound of formula (I) in a Lapatinib sample or a salt thereof having an unknown amount of this compound by means of HPLC;
ii) measuring the peak area corresponding to a "reference standard" containing a known amount of compound of formula (I) or a salt thereof by means of HPLC;
iii) defining the amount of compound of formula (I) in Lapatinib or a salt thereof comparing the area measured in step i) with that measured in step ii).

4. A method for identification and/or quantification of formula (I)

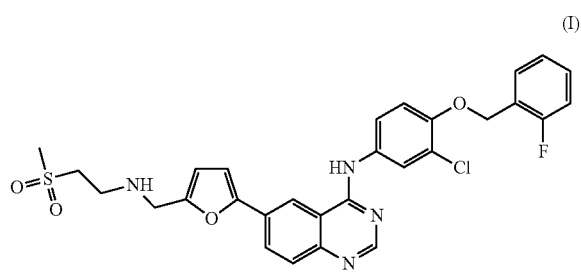 [SMILES: CS(=O)(=O)CCNCc1ccc(-c2ccc3ncnc(Nc4ccc(OCc5ccccc5F)c(Cl)c4)c3c2)o1]

in Lapatinib or a salt thereof comprising using formula (I) as a reference standard in a sample containing Lapatinib or a salt thereof.

* * * * *